United States Patent
Covarrubias et al.

(10) Patent No.: US 11,307,159 B2
(45) Date of Patent: Apr. 19, 2022

(54) IONIC-CONDUCTING RESISTOR FOR EXHAUST CONSTITUENT SENSORS

(71) Applicant: DELPHI TECHNOLOGIES IP LIMITED, St. Michael (BB)

(72) Inventors: Alfredo Ibarra Covarrubias, Oxford, MI (US); Kaius K. Polikarpus, Grand Blanc, MI (US)

(73) Assignee: DELPHI TECHNOLOGIES IP LIMITED, St. Michael (BB)

( * ) Notice: Subject to any disclaimer, the term of this patent is extended or adjusted under 35 U.S.C. 154(b) by 890 days.

(21) Appl. No.: 15/598,457

(22) Filed: May 18, 2017

(65) Prior Publication Data
US 2018/0335398 A1 Nov. 22, 2018

(51) Int. Cl.
*G01N 27/00* (2006.01)
*G01N 27/16* (2006.01)
*H01L 45/00* (2006.01)
*G01N 27/12* (2006.01)
*G01N 33/00* (2006.01)
*F01N 11/00* (2006.01)
*G01N 27/407* (2006.01)
*G01N 27/406* (2006.01)

(52) U.S. Cl.
CPC ........... *G01N 27/16* (2013.01); *F01N 11/007* (2013.01); *G01N 27/125* (2013.01); *G01N 27/4067* (2013.01); *G01N 27/4071* (2013.01); *G01N 33/0037* (2013.01); *G01N 33/0054* (2013.01); *H01L 45/08* (2013.01); *H01L 45/1226* (2013.01); *H01L 45/1266* (2013.01); *H01L 45/1286* (2013.01); *H01L 45/147* (2013.01); *F01N 2550/22* (2013.01); *F01N 2560/025* (2013.01); *F01N 2560/12* (2013.01)

(58) Field of Classification Search
CPC ... G01N 21/3504; G01N 27/124; G01N 31/10
USPC .......................................... 422/94, 83, 82.01
See application file for complete search history.

(56) References Cited

U.S. PATENT DOCUMENTS

| | | | |
|---|---|---|---|
| 2,673,228 A | 3/1954 | Kistler | |
| 3,768,157 A | 10/1973 | Buie | |
| 4,176,445 A | 12/1979 | Solow | |
| 4,233,033 A | 11/1980 | Eifler et al. | |
| 4,298,855 A | 11/1981 | Mills | |
| 4,385,611 A | 5/1983 | Harper et al. | |
| 5,389,218 A | 2/1995 | Bonne et al. | |
| 6,208,233 B1 | 3/2001 | Stein, Sr. et al. | |
| 7,135,891 B2 | 11/2006 | Grasso et al. | |
| 7,161,461 B1 | 1/2007 | Nelson | |
| 7,279,133 B2 | 10/2007 | Chen et al. | |
| 7,478,002 B2 | 1/2009 | Nelson et al. | |
| 2003/0209433 A1* | 11/2003 | LaBarge | C23C 14/083 204/426 |
| 2004/0094416 A1* | 5/2004 | Chen | G01N 27/419 204/426 |
| 2004/0095225 A1 | 5/2004 | Nelson | |
| 2005/0184851 A1 | 8/2005 | Nelson | |
| 2007/0146114 A1 | 6/2007 | Nelson | |
| 2011/0214988 A1 | 9/2011 | Yoshida et al. | |

FOREIGN PATENT DOCUMENTS

| | | |
|---|---|---|
| CA | 1127870 A1 | 7/1982 |
| GB | 2005025 A | 4/1979 |
| JP | 07226301 A | 8/1995 |
| JP | 09232118 A | 9/1997 |
| JP | 2001305100 A | 10/2001 |
| JP | 2015068820 A | 4/2015 |

* cited by examiner

*Primary Examiner* — Natalia Levkovich
(74) *Attorney, Agent, or Firm* — Joshua M. Haines

(57) ABSTRACT

A resistor-assembly includes a substrate, a heater, a resistor-element, and conductive-leads. The substrate is formed of a ceramic-material. The heater heats the resistor-assembly. The resistor-element is formed of an ion-conducting material that overlies the substrate. The conductive-leads are formed of a catalytic-metal that are in communication with a gas and in electrical contact with the resistor-element. The resistor-element is characterized by a resistance-value influenced by an oxygen-presence in the gas when the resistor-element is heated by the heater such that a resistor-temperature is greater than a temperature-threshold.

15 Claims, 5 Drawing Sheets

IONIC-CONDUCTING RESISTOR FOR EXHAUST CONSTITUENT SENSORS

TECHNICAL FIELD OF INVENTION

This disclosure generally relates to a resistor-assembly, and more particularly relates to a resistor-assembly suitable for use on a gas-sensing-device.

BACKGROUND OF INVENTION

It is known to use a trim-resistor to adjust an output of a gas-sensor to mitigate the part-to-part variation inherent in a mass produced component. The trim-resistor may be integrated into the sensing-circuitry of the gas-sensor, or may be a separate circuit.

SUMMARY OF THE INVENTION

In accordance with one embodiment, a resistor-assembly is provided. The resistor-assembly includes a substrate, a heater, a resistor-element, and conductive-leads. The substrate is formed of a ceramic-material. The heater heats the resistor-assembly. The resistor-element is formed of an ion-conducting material that overlies the substrate. The conductive-leads are formed of a catalytic-metal that are in communication with a gas and in electrical contact with the resistor-element. The resistor-element is characterized by a resistance-value influenced by an oxygen-presence in the gas when the resistor-element is heated by the heater such that a resistor-temperature is greater than a temperature-threshold.

In another embodiment, a gas-sensing-device suitable for use to control an internal combustion engine is provided. The gas-sensing-device includes a substrate, a heater, a sensing-element, a resistor-element, and conductive-leads. The substrate is formed of a ceramic-material. The heater is in thermal communication with the substrate and heats the device in response to receiving electrical energy. The sensing-element is in thermal communication with the heater. The sensing-element detects oxygen in an exhaust-stream. The sensing-element outputs a sensing-signal based on a concentration of the oxygen in the exhaust-stream when the sensing-element is heated to a sensing-temperature greater than a temperature-threshold. The resistor-element is in thermal communication with the heater. The resistor-element is formed of an ion-conducting material that overlies the substrate. The conductive-leads are formed of a catalytic-metal that are in communication with a gas and in electrical contact with the resistor-element. The resistor-element is characterized by a resistance-value influenced by an oxygen-presence in the gas when the resistor-element is heated by the heater such that a resistor-temperature is greater than the temperature-threshold. The concentration of the oxygen is indicated based on the resistance-value and the sensing-signal.

Further features and advantages will appear more clearly on a reading of the following detailed description of the preferred embodiment, which is given by way of non-limiting example only and with reference to the accompanying drawings.

BRIEF DESCRIPTION OF DRAWINGS

The present invention will now be described, by way of example with reference to the accompanying drawings, in which.

The reference numbers of similar elements in the embodiments shown in the various figures share the last two digits.

DETAILED DESCRIPTION

Figure 1:
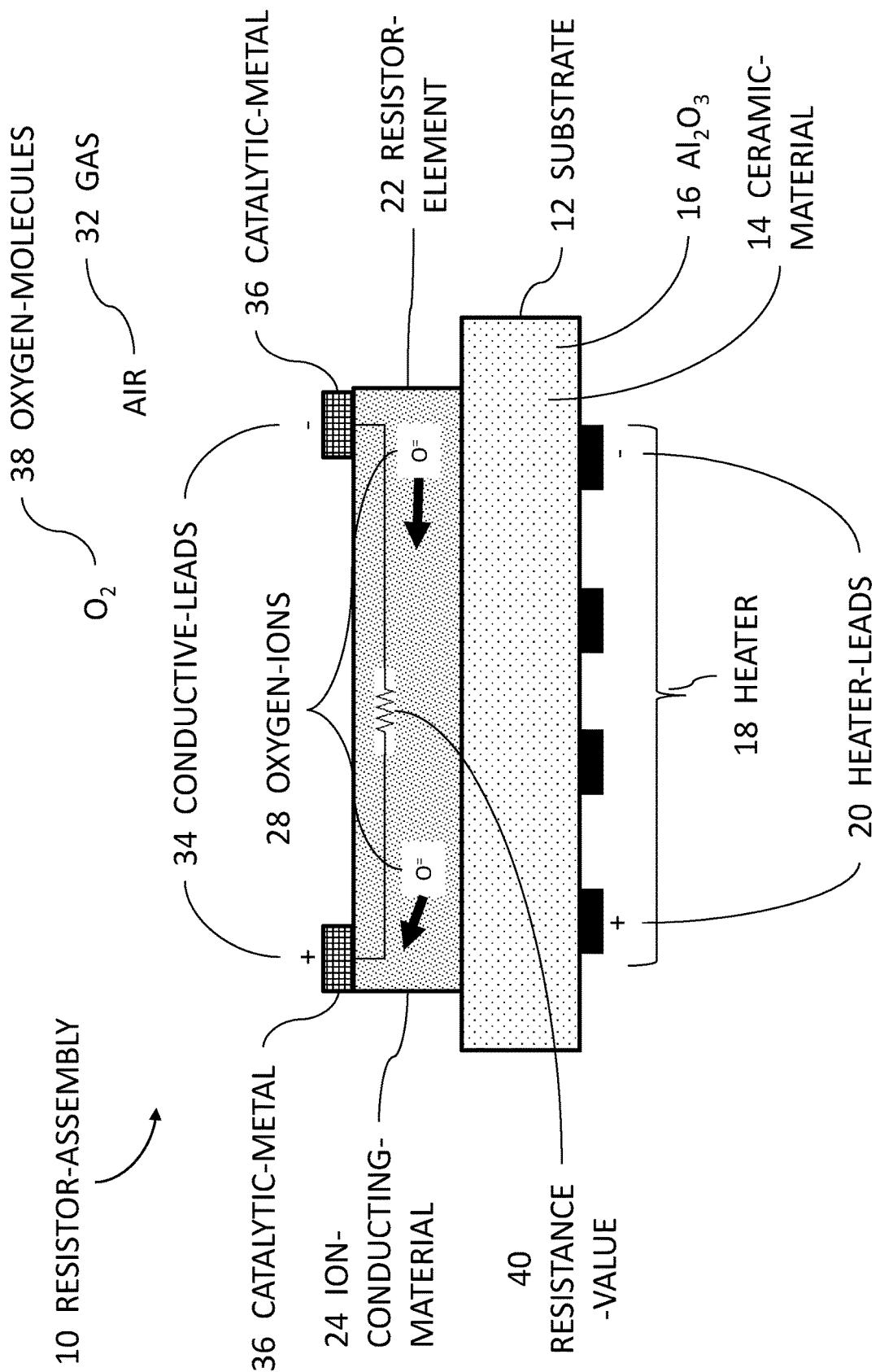
FIG. 1 is a cross section view of a resistor-assembly in accordance with one embodiment.

FIG. 1 illustrates a non-limiting example of a cross section view of a resistor-assembly 10, suitable for use as a trim-resistor on a gas-sensor. The resistor-assembly 10 includes a substrate 12 formed of a ceramic-material 14. The ceramic-material 14 may include an aluminum oxide 16 ($Al_2O_3$ 16) with other elements added to the $Al_2O_3$ 16 for processing and functional requirements, as will be recognized by one skilled in the art. The substrate may be used to support circuitry and components of the resistor-assembly 10, as will be described below.

The resistor-assembly 10 also includes a heater 18 that heats the resistor-assembly 10. The heater 18 overlies the substrate 12 and may be applied directly to the substrate 12 by known methods that include, but are not limited to, screen printing, pad-printing, stenciling, etc. The heater 18 may include a serpentine-pattern to concentrate heat in a particular area of the resistor-assembly 10. The heater 18 may also include heater-leads 20 that may be used to electrically connect the heater 18 to a power-source (not shown). The heater 18 may be formed of a thick-film ink material such as CN38-019B from Ferro Corporation of Mayfield Heights, Ohio, USA, and processed according to the manufacturer's recommendations.

The resistor-assembly 10 also includes a resistor-element 22 that overlies the substrate 12. The resistor-element 22 is formed of an ion-conducting material 24 that may include an oxide of an element selected from a list that includes zirconium (Zr), cerium (Ce), and uranium (U), and Thorium (Th). In contrast to an electron-conducting material (not shown), the ion-conducting material 24 conducts ions of a particular element in order to conduct electricity. The ion-conducting material 24 is preferably zirconia that may be stabilized with oxides of other elements including, but not limited to yttrium and/or scandium. The ion-conducting material 24 is more preferably a yttria stabilized zirconia (YSZ) that includes yttria in concentrations between 1 mol % and 10 mol %, and preferably in concentrations between 4 mol % and 7 mol %. The properties of YSZ are such that it may conduct oxygen-ions 28 when heated to a temperature above a temperature-threshold 30, and when supplied by a source of oxygen, such as a gas 32 that contains oxygen (e.g. air). The temperature-range in which YSZ conducts ions is understood by those skilled in the art to be between 300° C. and 1100° C. It will also be recognized by those in the art that a rate of ion conduction increases as the temperature of the YSZ increases. Empirical testing has indicated that the temperature-threshold 30 of 700° C. provides for a good balance between ion conduction and durability of the resistor-assembly 10. The resistor-element 22 may be may be applied directly to the substrate 12 by known methods that include, but are not limited to, screen printing, pad-printing, stenciling, etc. The resistor-element 22 may be formed of a thick-film ink that is manufactured by any of the known commercial ink manufacturers (e.g. Ferro Corp., Heraeus, Dupont, ESL, etc.) and processed according to the manufacturer's recommendations.

The resistor-assembly 10 also includes conductive-leads 34 that may be formed of a catalytic-metal 36 including platinum (Pt), palladium (Pd), rhodium (Rh), silver (Ag), nickel (Ni), gold (Au), and their alloys. The conductive-leads 34 may be in communication with the gas 32 wherein the properties of the catalytic-metal 36 may reduce oxygen-molecules 38 to oxygen-ions 28 at the interface between the conductive-lead 34 and the resistor-element 22. The conductive-leads 34 may also be in electrical contact with the resistor-element 22 to enable the resistor-element 22 to be characterized by a resistance-value 40 that may be influenced by an oxygen-presence in the gas 32. The resistance-value 40 may be determined when the resistor-element 22 is heated by the heater 18 such that a resistor-temperature 26 is greater than the temperature-threshold 30. The conductive-leads 34 may be may be applied by known methods that include, but are not limited to, screen printing, pad-printing, stenciling, etc. The conductive-leads 34 may be formed of a thick-film ink material such as CN38-301 from Ferro Corporation of Mayfield Heights, Ohio, USA, and processed according to the manufacturer's recommendations.

Figure 2:
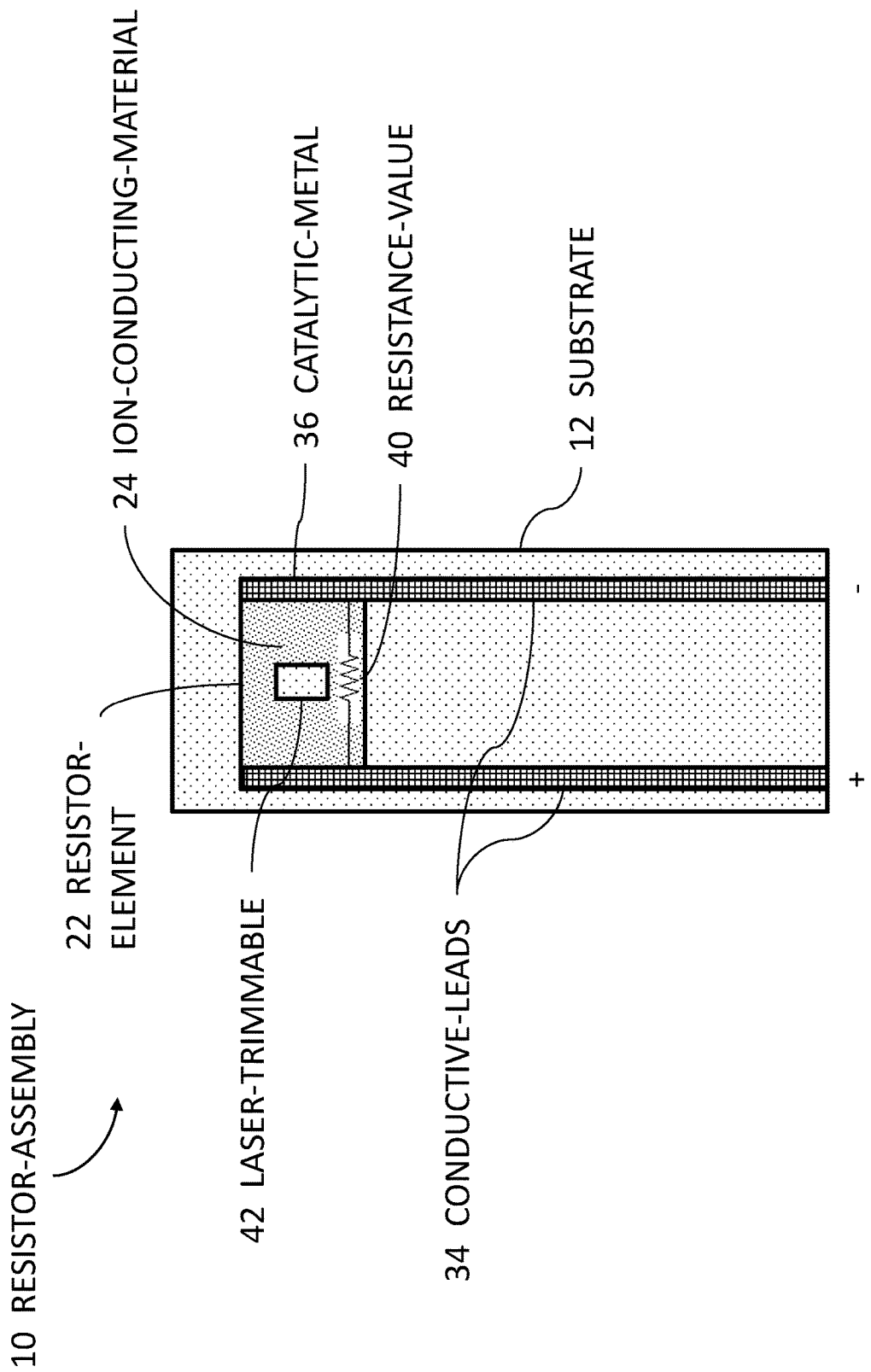
FIG. 2 is a top view of the resistor-assembly of FIG. 1 in accordance with one embodiment.

The resistor-element 22 may also be laser-trimmable 42 such that the resistor-assembly 10 may be adjusted to a predetermined resistance-value 40. FIG. 2 illustrates a top view of the resistor-assembly 10 where the laser-trimming operation has removed a portion of the resistor-element 22 and exposes a portion of the substrate 12. One skilled in the art will recognize that the laser-trimming 42 reduces a cross sectional area of the resistor-element 22 that increases the resistance-value 40. The laser-trimming 42 operation may advantageously be conducted when the resistor-assembly 10 is heated to the temperature above the temperature-threshold 30. This is beneficial because the resistance-value 40 may be more precisely adjusted at the temperature at which the resistor-assembly 10 may operate.

Figure 3:
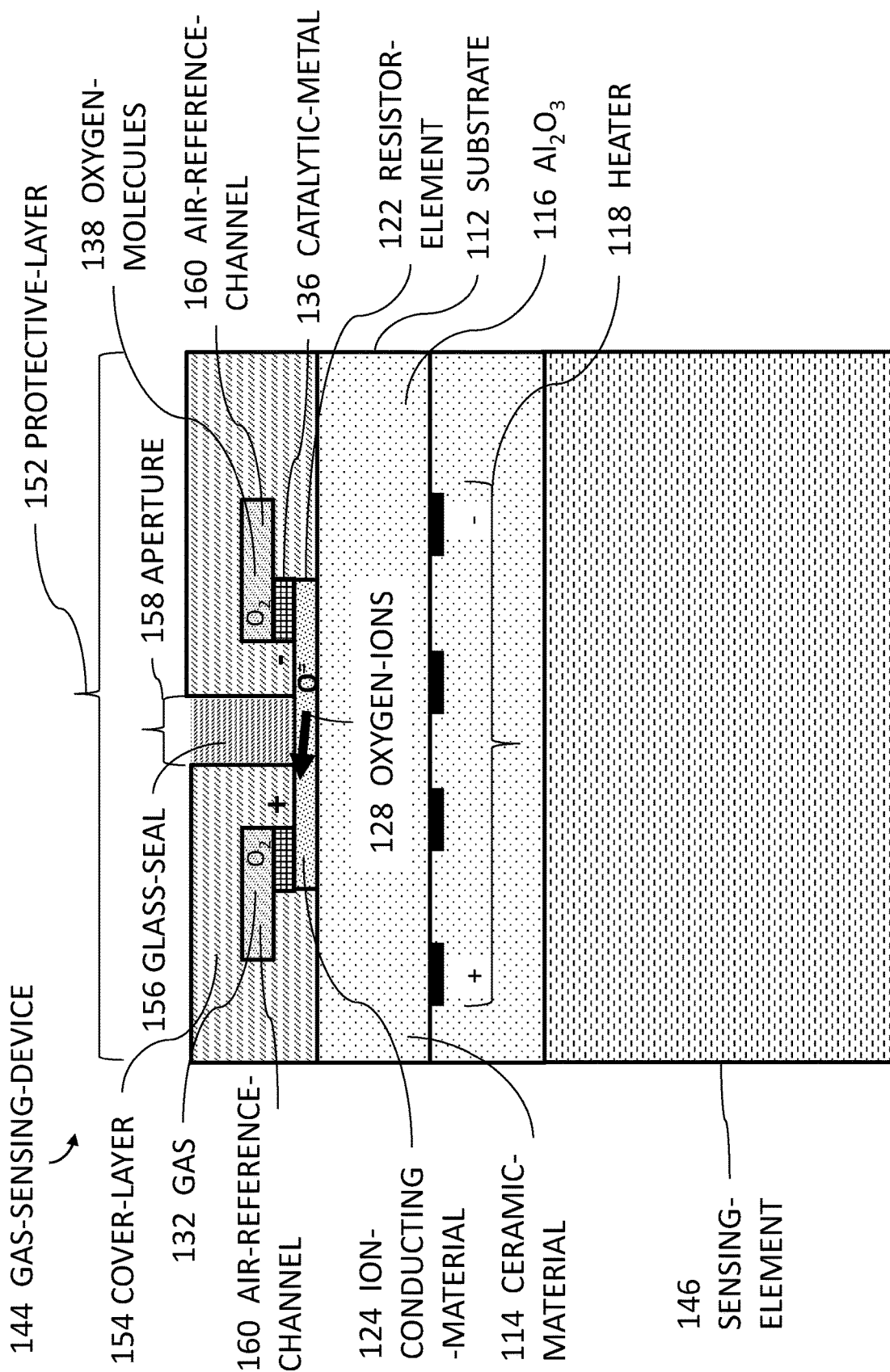
FIG. 3 is a cross section view of a gas-sensing-device in accordance with one embodiment.

FIG. 3 illustrates a non-limiting example of a gas-sensing-device 144, hereafter referred to as the device 144, suitable for use to control an internal combustion engine (not shown). The device 144 may sense gas-species including oxygen, oxides of nitrogen (NOx), and ammonia, and may use different catalytic-electrodes (not shown) selected to react with the particular gas-species being detected. For the purposes of illustration, FIG. 3 includes a wide-range-air fuel oxygen sensor (WRAF-sensor), also known as a wide-band sensor, linear oxygen sensor, air-fuel ratio sensor, universal exhaust gas oxygen sensor (UEGO), and wide-band lambda sensor, and is not intended to limit the invention to only the WRAF-sensor.

The device 144 includes a substrate 112 formed of a ceramic-material 114. The ceramic-material 114 may include an aluminum oxide 116 ($Al_2O_3$ 116) with other elements added to the $Al_2O_3$ 116 for processing and functional requirements, as will be recognized by one skilled in the art. The substrate 112 may be used to support circuitry and components of the device 144, as will be described below.

The device 144 also includes a heater 118 in thermal communication with the substrate 112 that heats the device 144 in response to receiving electrical energy (not shown). The heater 118 overlies the substrate 112 and may be applied directly to the substrate 112 by known methods that include, but are not limited to, screen printing, pad-printing, stencil-ing, etc. The heater 118 may include a serpentine-pattern (FIG. 5) to concentrate heat in a particular area of the device 144, such as a sensing-end (not specifically shown). The heater 118 may also include heater-leads 120 (FIG. 5) that may be used to electrically connect the heater 118 the electrical energy. The heater 18 may be formed of a thick-film ink material such as CN38-019B from Ferro Corporation of Mayfield Heights, Ohio, USA, and processed according to the manufacturer's recommendations.

The device 144 also includes a sensing-element 146 in thermal communication with the heater 118. The sensing-element 146 may detect oxygen in an exhaust-stream (not shown) and outputs a sensing-signal 148 (FIG. 5) based on a concentration of the oxygen in the exhaust-stream, when the sensing-element 146 is heated to a sensing-temperature 150 greater than a temperature-threshold 130.

The device 144 also includes a resistor-element 122 (FIGS. 3-5) that overlies the substrate 112. The resistor-element 122 is formed of an ion-conducting material 124 that may include an oxide of an element selected from a list that includes zirconium (Zr), cerium (Ce), uranium (U), and thorium (Th). In contrast to an electron-conducting material (not shown), the ion-conducting material 124 conducts ions of a particular element in order to conduct electricity. The ion-conducting material 124 is preferably zirconia that may be stabilized with oxides of other elements including, but not limited to yttrium and/or scandium. The ion-conducting material 124 is more preferably a yttria stabilized zirconia (YSZ) that includes yttria in concentrations between 1 mol % and 10 mol %, and preferably in concentrations between 4 mol % and 7 mol %. The properties of YSZ are such that it may conduct oxygen-ions 128 when heated to the temperature above the temperature-threshold 130, and when supplied by a source of oxygen, such as a gas 132 that contains oxygen (e.g. air). The temperature-range in which YSZ conducts ions is understood by those skilled in the art to be between 300° C. and 1100° C. It will also be recognized by those in the art that a rate of ion conduction increases as the temperature of the YSZ increases. Empirical testing has indicated that the temperature-threshold 130 of 700° C. provides for a good balance between ion conduction and durability of the device 144. The resistor-element 122 may be may be applied directly to the substrate 112 by known methods that include, but are not limited to, screen printing, pad-printing, stenciling, etc. The resistor-element 122 may be formed of a thick-film ink that is manufactured by any of the known commercial ink manufacturers (e.g. Ferro Corp., Heraeus, Dupont, ESL, etc.) and processed according to the manufacturer's recommendations.

The device 144 also includes conductive-leads 134 that may be formed of a catalytic-metal 136 including platinum (Pt), palladium (Pd), rhodium (Rh), silver (Ag), nickel (Ni), gold (Au), and their alloys. The conductive-leads 134 may be in communication with the gas 132 wherein the properties of the catalytic-metal 136 may reduce oxygen-molecules 138 to oxygen-ions 128 at the interface between the conductive-lead 134 and the resistor-element 122. The conductive-leads 134 may also be in electrical contact with the resistor-element 122 to enable the resistor-element 122 to be characterized by a resistance-value 140 that may be influenced by an oxygen-presence in the gas 132. The resistance-value 140 may be determined when the resistor-element 122 is heated by the heater 118 such that a resistor-temperature 126 (FIG. 5) is greater than the temperature-threshold 130, whereby the concentration of the oxygen in the exhaust-stream is indicated based on the resistance-value 140 and the sensing-signal 148. The conductive-leads 134 may be applied by known methods that include, but are not limited to, screen printing, pad-printing, stenciling, etc. The conductive-leads 134 may be formed of a thick-film ink material such as CN38-301 from Ferro Corporation of Mayfield Heights, Ohio, USA, and processed according to the manufacturer's recommendations.

Figure 4:
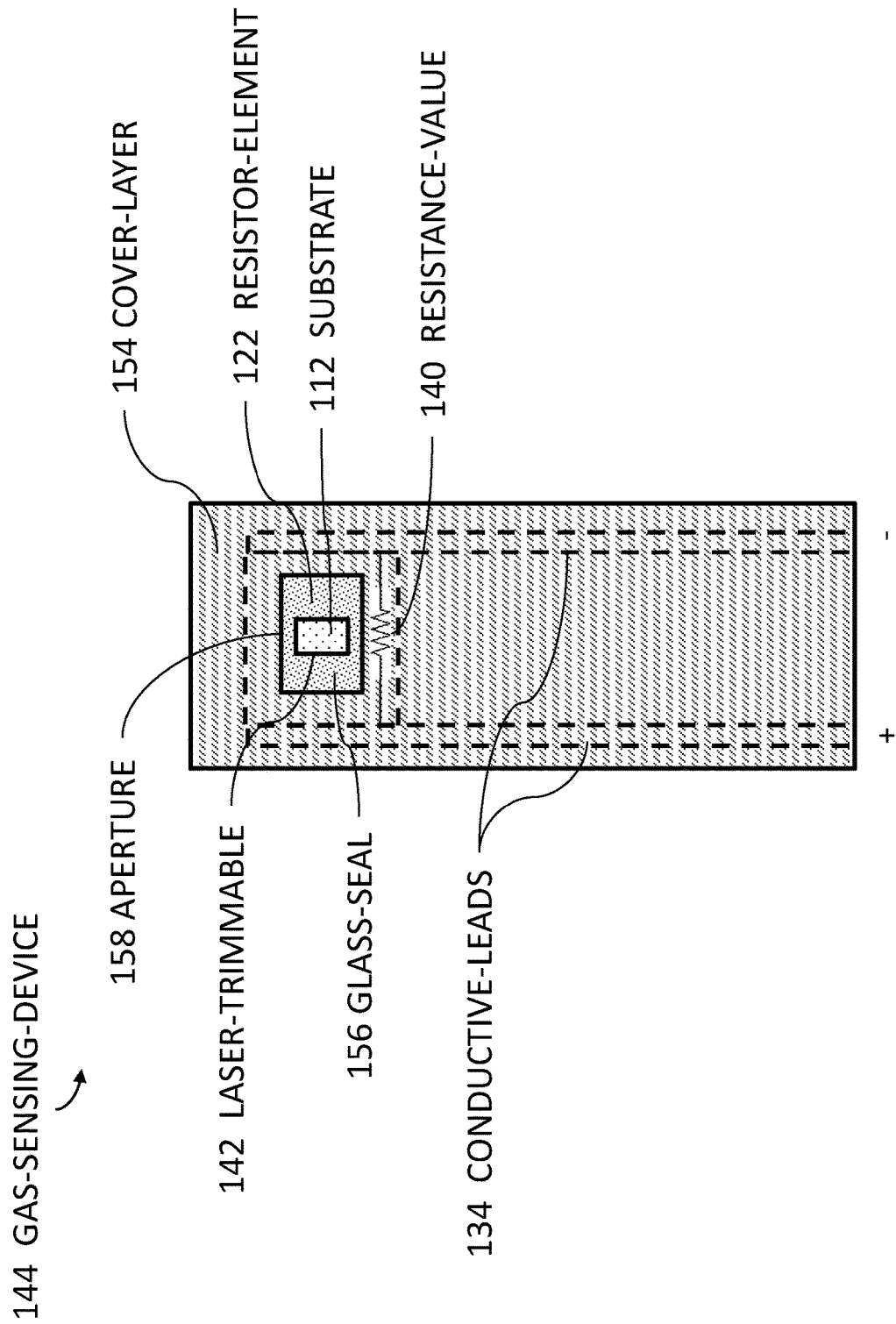
FIG. 4 is a top view of the gas-sensing-device of FIG. 3 in accordance with one embodiment.

The resistor-element 122 may also be laser-trimmable 142 such that the resistor-element 122 may be adjusted to a predetermined resistance-value 140. FIG. 4 illustrates a top view of the device 144 where the laser-trimming 142 operation has removed a portion of the resistor-element 122 and exposes a portion of the substrate 112. One skilled in the art will recognize the laser-trimming 142 reduces a cross sectional area of the resistor-element 122 that increases the resistance-value 140. The laser-trimming 142 operation may advantageously be conducted when the device 144 is heated to the temperature above the temperature-threshold 130. This is beneficial because the resistance-value 140 may be more precisely adjusted at the temperature at which the device 144 may operate.

The resistor-element 122 may be protected from the environment (e.g. exhaust gasses) by covering the resistor-element 122 with a protective-layer 152 compatible with the substrate 112. FIGS. 3-4 illustrate the resistor-element 122 overlaid with a cover-layer 154, and a glass-seal 156 that may be dispensed into an aperture 158 defined by the cover-layer 154. The cover-layer 154 with the aperture 158 advantageously exposes a portion of the resistor-element 122 to enable the laser-trimming 142 operation on the assembled device 144, after which the glass-seal 156 may be dispensed into the aperture 158 to complete the protective-layer 152.

Figure 5:
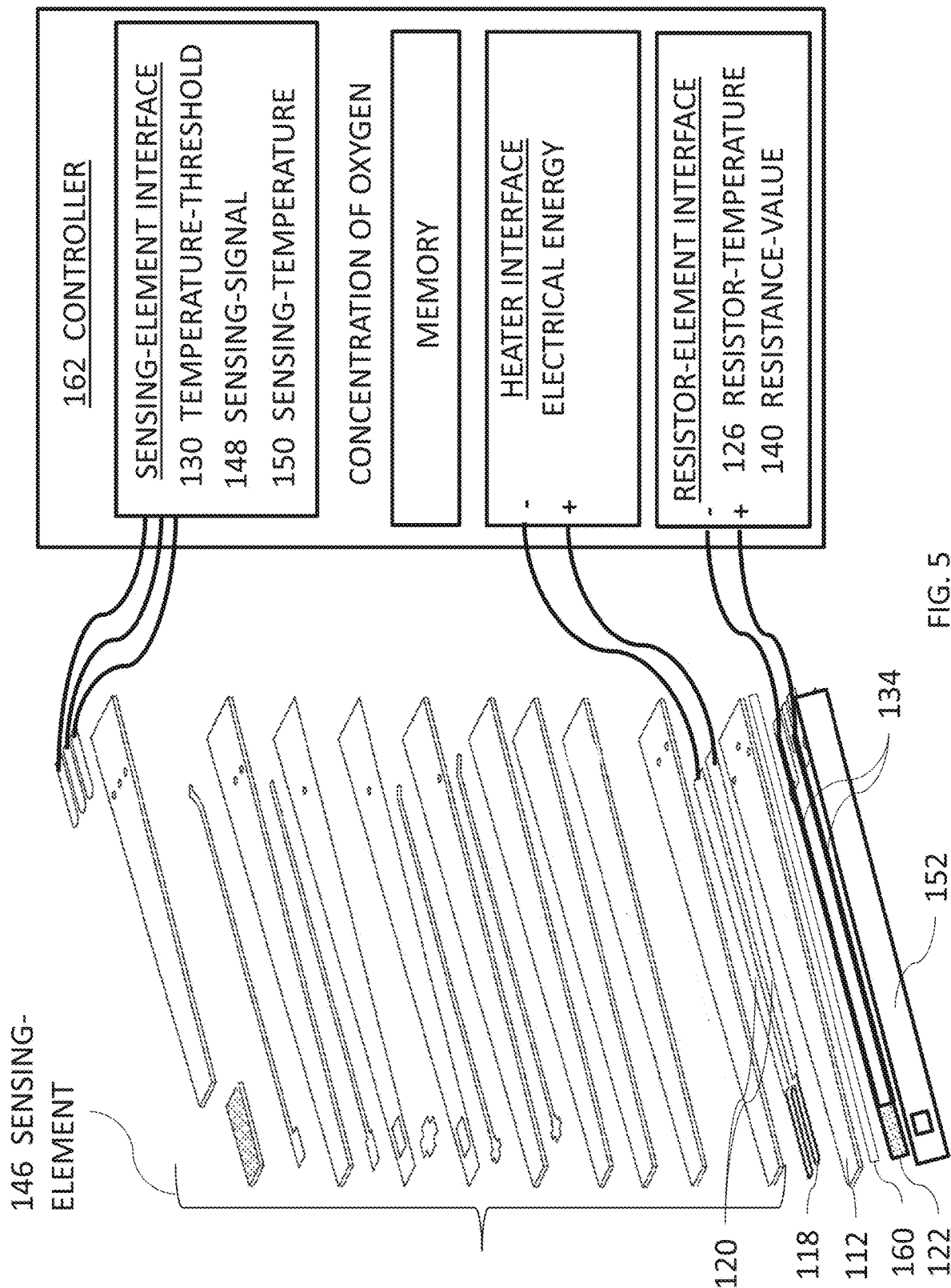
FIG. 5. is an illustration of a controller for the gas-sensing-device of FIG. 3 in accordance with one embodiment.

FIGS. 3 and 5 also illustrate an air-reference-channel 160 interposed between the cover-layer 154 and the conductive-leads 134 that extends along a longitudinal-axis (not specifically shown) of the device 144. The air-reference-channel 160 may provide the source of oxygen to the conductive-leads 134 by channeling the gas 132 through the device 144 to the catalytic-metal 136 of the conductive-leads 134. The air-reference-channel 160 may be in direct communication with the source of air external to the device 144, or may be in communication with another source of oxygen that may be included in the device 144.

The device 144 may also include a controller 162 (FIG. 5) in electrical communication with the heater 118, the sensing-element 146, and the resistor-element 122. The controller 162 may include a processor (not specifically shown) such as a microprocessor or other control circuitry such as analog and/or digital control circuitry including an application specific integrated circuit (ASIC) for processing data as should be evident to those in the art. The controller 162 may include a memory (not specifically shown), including non-volatile memory, such as electrically erasable programmable read-only-memory (EEPROM) for storing one or more routines, thresholds, and captured data. The one or more routines may be executed by the processor to perform steps for operating the device 144 based on signals received by the controller 162 as described herein.

The controller 162 may control the electrical energy supplied to the heater 118 to maintain the temperature of the device 144. The device 144 may become active above the temperature of 400° C. and is preferably maintained at the temperature above the temperature-threshold 130. The electrical energy may be controlled by any of the known methods including, but not limited to, a high-side-driver (not shown) or a low-side-driver (not shown) using a pulse-width-modulated signal (not shown). A temperature-feedback signal (not shown) may be used by the controller 162 to control the temperature of the device 144 and may include an impedance (not shown) of the sensing-element 146.

The controller 162 may also determine the resistance-value 140 of the resistor-element 122 when the device 144 is heated to the temperature above the temperature-threshold 130. The controller 162 may use any of the known methods to determine the resistance-value 140 that will be apparent to one skilled in the art, and may include an analog to digital converter (ADC, not shown) that may be included in the controller 162.

The controller 162 may also determine the sensing-signal 148 of the sensing-element 146 when the device 144 is heated to the temperature above the temperature-threshold 130. The controller 162 may use an ASIC designed specifically for the purpose of determining the sensing-signal 148, as will be evident to one skilled in the art. The sensing-signal 148 may be a voltage or a current that may be measured by another ADC (not shown) that may be included in the controller 162, and may be configured to measure the voltage or the current.

The controller 162 may also indicate the concentration of the oxygen in the exhaust-stream based on the resistance-value 140 and the sensing-signal 148 through software and/or routines stored in the memory of the controller 162, as will be understood by one skilled in the art.

Accordingly, a resistor-assembly 10, a gas-sensing-device 144, and a controller 162 for the gas-sensing-device 144 is provided. The resistor-assembly 10 is capable of operating at high temperatures that are typical in the exhaust of the internal combustion engine. The gas-sensing-device 144 is configured such that the resistor-element 122 is laser-trimmable 142 at the temperature the gas-sensing-device 144 may operate, which enables greater accuracy in correcting the concentration of oxygen in the exhaust-stream.

While this invention has been described in terms of the preferred embodiments thereof, it is not intended to be so limited, but rather only to the extent set forth in the claims that follow. While this invention has been described in terms of the preferred embodiments thereof, it is not intended to be so limited, but rather only to the extent set forth in the claims that follow. Moreover, the use of the terms first, second, etc. does not denote any order of importance, but rather the terms first, second, etc. are used to distinguish one element from another. Furthermore, the use of the terms a, an, etc. do not denote a limitation of quantity, but rather denote the presence of at least one of the referenced items. Additionally, directional terms such as upper, lower, etc. do not denote any particular orientation, but rather the terms upper, lower, etc. are used to distinguish one element from another and locational establish a relationship between the various elements.

We claim:

1. A resistor-assembly, comprising:
a substrate formed of a ceramic-material;
a heater that heats the resistor-assembly;
a resistor-element formed of an ion-conducting material that has a resistance-value which is influenced by an oxygen-presence in a gas when the resistor-element is heated by the heater above a temperature-threshold, wherein the resistor-element overlies the substrate, and wherein said substrate is located between the heater and the resistor-element; and
conductive-leads formed of a catalytic-metal that are in communication with the gas and in electrical contact with the resistor-element.

2. The resistor-assembly in accordance with claim 1, wherein the resistor-element conducts oxygen-ions when the resistor-element is heated above the temperature-threshold.

3. The resistor-assembly in accordance with claim 2, wherein the ion-conducting material includes an oxide of an element selected from a list that includes zirconium (Zr), cerium (Ce), uranium (U), and thorium (Th).

4. The resistor-assembly in accordance with claim 1, wherein the ceramic-material includes an aluminum oxide.

5. The resistor-assembly in accordance with claim 1, wherein the catalytic-metal includes platinum (Pt), palladium (Pd), rhodium (Rh), silver (Ag), nickel (Ni), gold (Au), and alloys thereof.

6. A gas-sensing-device suitable for use to control an internal combustion engine, said device comprising:
   a substrate formed of a ceramic-material;
   a heater which heats the device in response to receiving electrical energy;
   a sensing-element in thermal communication with the heater, wherein the sensing-element detects oxygen in an exhaust-stream and outputs a sensing-signal based on a concentration of the oxygen in the exhaust-stream;
   a resistor-element in thermal communication with the heater, said resistor-element formed of an ion-conducting material that has a resistance-value which is influenced by an oxygen-presence in a gas when the resistor-element is heated by the heater above a temperature-threshold, wherein the resistor-element overlies the substrate, and wherein said substrate is located between the heater and the resistor-element; and
   conductive-leads formed of a catalytic-metal that are in communication with the gas and in electrical contact with the resistor-element, whereby the concentration of the oxygen in the exhaust-stream is indicated based on the resistance-value and the sensing-signal.

7. The device in accordance with claim 6, wherein the device includes a controller in electrical communication with the heater, the sensing-element, and the resistor-element, said controller controls the electrical energy supplied to the heater, determines the resistance-value of the resistor-element, determines the sensing-signal of the sensing-element, and indicates the concentration of the oxygen in the exhaust-stream.

8. The device in accordance with claim 6, wherein the resistor-element conducts oxygen-ions when the resistor-element is heated above the temperature-threshold.

9. The device in accordance with claim 8, wherein the ion-conducting material includes an oxide of an element selected from a list consisting of zirconium (Zr), cerium (Ce), uranium (U), and thorium (Th).

10. The device in accordance with claim 6, wherein the ceramic-material includes an aluminum oxide.

11. The device in accordance with claim 6, wherein the catalytic-metal includes platinum (Pt), palladium (Pd), rhodium (Rh), silver (Ag), nickel (Ni), gold (Au) and alloys thereof.

12. The device in accordance with claim 6, further comprising a protective-layer which overlays the resistor-element, the protective-layer including a cover-layer with an aperture extending therethrough such that the aperture is aligned with the resistor-element.

13. The device of claim 12, wherein the protective-layer also includes a glass-seal within the aperture.

14. The device of claim 13, wherein:
   the cover-layer contacts the resistor-element and the substrate; and
   the glass-seal contacts the resistor-element.

15. The device of claim 6, wherein the conductive leads are exposed to a channel which contains the gas.

* * * * *